US00PP27961P2

(12) United States Plant Patent
Moen

(10) Patent No.: US PP27,961 P2
(45) Date of Patent: May 2, 2017

(54) ***GERBERA* PLANT NAMED 'GARKENDALL'**

(50) Latin Name: *Gerbera hybrida*
Varietal Denomination: Garkendall

(71) Applicant: Melchior Moen, Mijdrecht (NL)

(72) Inventor: Melchior Moen, Mijdrecht (NL)

(73) Assignee: Florist Holland B.V., Aalsmeer (NL)

( * ) Notice: Subject to any disclaimer, the term of this patent is extended or adjusted under 35 U.S.C. 154(b) by 93 days.

(21) Appl. No.: 14/545,049

(22) Filed: Mar. 19, 2015

(51) Int. Cl.
*A01H 5/02* (2006.01)

(52) U.S. Cl.
USPC ..... Plt./357

(58) Field of Classification Search
USPC ..... Plt./357
See application file for complete search history.

(56) References Cited

PUBLICATIONS

Florist Breeding & propagation Catalogue 2014/2015. website https://issuu.com/martinew/docs/website_catalogus. 5 pages.*

* cited by examiner

*Primary Examiner* — Susan McCormick Ewoldt
*Assistant Examiner* — Karen Redden
(74) *Attorney, Agent, or Firm* — C. A. Whealy

(57) ABSTRACT

A new and distinct cultivar of *Gerbera* plant named 'Garkendall', characterized by its compact, broadly upright and uniformly mounding plant habit; dense and bushy appearance; numerous inflorescences with dark orange red-colored ray florets; upright and strong scapes; and good garden performance and relatively tolerant to cold temperatures.

1 Drawing Sheet

Botanical designation: *Gerbera hybrida.*
Cultivar denomination: 'GARKENDALL'.

BACKGROUND OF THE INVENTION

The present invention relates to a new and distinct cultivar of *Gerbera* plant, botanically known as *Gerbera hybrida* and hereinafter referred to by the cultivar name 'Garkendall'.

The new *Gerbera* plant is a product of a planned breeding program conducted by the Inventor in De Kwakel, The Netherlands. The objective of the breeding program is to create new compact garden *Gerbera* plants with numerous attractive inflorescences, resistant to cold temperatures and good garden performance.

The new *Gerbera* plant originated from a cross-pollination made during the spring of 2010 in De Kwakel, The Netherlands of a proprietary selection of *Gerbera hybrida* identified as code number 09T231, not patented, as the female, or seed, parent with a proprietary selection of *Gerbera hybrida* identified as code number 09T193, not patented, as the male, or pollen, parent. The new *Gerbera* plant was discovered and selected by the Inventor as a single flowering plant within the progeny of the stated cross-pollination in a controlled greenhouse environment in De Kwakel, The Netherlands during the summer of 2011.

Asexual reproduction of the new *Gerbera* plant by cuttings in a controlled environment in De Kwakel, The Netherlands since the summer of 2011 has shown that the unique features of this new *Gerbera* plant are stable and reproduced true to type in successive generations.

SUMMARY OF THE INVENTION

Plants of the new *Gerbera* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Garkendall'. These characteristics in combination distinguish 'Garkendall' as a new and distinct *Gerbera* plant:

1. Compact, broadly upright and uniformly mounding plant habit.
2. Dense and bushy appearance.
3. Numerous inflorescences with dark orange red-colored ray florets.
4. Upright and strong scapes.
5. Good garden performance and relatively tolerant to cold temperatures.

Plants of the new *Gerbera* differ from plants of the female parent selection in the following characteristics:

1. Plants of the new *Gerbera* have slightly smaller inflorescences than plants of the female parent selection.
2. Plants of the new *Gerbera* and the female parent selection differ in ray floret color as plants of the female parent selection have lighter orange red-colored ray florets.

Plants of the new *Gerbera* differ from plants of the male parent selection in the following characteristics:

1. Plants of the new *Gerbera* have slightly smaller inflorescences than plants of the male parent selection.
2. Plants of the new *Gerbera* and the male parent selection differ in ray floret color as plants of the male parent selection have yellow-colored ray florets.

Plants of the new *Gerbera* can be compared to plants of the *Gerbera hybrida* 'Garsophie Imp.', disclosed in U.S. Plant Pat. No. 25,960. Plants of the new *Gerbera* differ from plants of 'Garsophie Imp.' in the following characteristics:

1. Plants of the new *Gerbera* have shorter leaves than plants of 'Garsophie Imp.'.
2. Inflorescences of plants of the new *Gerbera* have broader ray florets than inflorescences of plants of 'Garsophie Imp.'.
3. Plants of the new *Gerbera* and 'Garsophie Imp.' differ in ray floret apex shape as ray florets of 'Garsophie Imp.' have less rounded apices.
4. Plants of the new *Gerbera* and 'Garsophie Imp.' differ slightly in ray floret color as plants of 'Garsophie Imp.' have red-colored ray florets.

BRIEF DESCRIPTION OF THE PHOTOGRAPHS

The accompanying photograph illustrates the overall appearance of the new *Gerbera* plant showing the colors as true as it is reasonably possible to obtain in colored reproductions of this type. Colors in the photograph may differ slightly from the color values cited in the detailed botanical description which accurately describe the colors of the new *Gerbera* plant.

The photograph comprises a side perspective view of a typical flowering plant of 'Garkendall' grown in a container.

DETAILED BOTANICAL DESCRIPTION

The aforementioned photographs and following observations and measurements describe plants grown during the autumn and winter in 15-cm containers in a glass-covered greenhouse in De Kwakel, The Netherlands and under cultural practices typical of commercial garden *Gerbera* production. During the production of the plants, day temperatures ranged from 10° C. to 16° C. and night temperatures averaged 10° C. Plants were six months old when the photographs were taken and 17 weeks old when the description was taken. In the following description, color references are made to The Royal Horticultural Society Colour Chart, 2007 Edition, except where general terms of ordinary dictionary significance are used.

Botanical classification: *Gerbera hybrida* 'Garkendall'.

Parentage:

*Female, or seed, parent*.—Proprietary selection of *Gerbera hybrida* identified as code number 09T231, not patented.

*Male, or pollen, parent*.—Proprietary selection of *Gerbera hybrida* identified as code number 09T193, not patented.

Propagation:

*Type*.—By cuttings and by tissue culture.

*Time to initiate roots, by cuttings, summer and winter*.—About 3.5 weeks at temperatures about 20° C.

*Time to initiate roots, by tissue culture, summer and winter*.—About 2.5 to 3 weeks at temperatures about 20° C.

*Time to produce a rooted young plant, by cuttings, summer and winter*.—About 3.5 weeks at temperatures about 20° C. to 26° C.

*Time to produce a rooted young plant, by tissue culture, summer and winter*.—About five to six weeks at temperatures about 20° C.

*Root description*.—Fibrous; white in color.

Plant description:

*Appearance*.—Herbaceous perennials that are typically grown as container or garden plants; compact and uniformly mounding plant habit, broadly upright and roughly globular in shape; numerous leaves arranged in basal rosettes and outwardly arching; dense and bushy habit; inflorescences held above the foliar plane on erect and strong basal scapes; low vigor to moderately vigorous growth habit.

*Plant height, soil level to top of foliar plane*.—About 15.8 cm.

*Plant height, soil level to top of inflorescences*.—About 33.1 cm.

*Plant width*.—About 35.4 cm.

Leaf description:

*Arrangement*.—Alternate, simple.

*Length*.—About 13.6 cm.

*Width*.—About 6.4 cm.

*Shape*.—Obovate to narrowly obovate; runcinate; slightly curved.

*Apex*.—Obtuse.

*Base*.—Acuminate.

*Margin*.—Coarsely and irregularly angulate; sinuses divergent; undulate.

*Texture, upper surface*.—Sparsely pubescent along main vein.

*Texture, lower surface*.—Densely tomentose.

*Venation pattern*.—Pinnate.

*Color*.—Developing leaves, upper surface: Darker than between N137C and 141A. Developing leaves, lower surface: Close to 138B. Fully expanded leaves, upper surface: Close to N137A; venation, close to 143C. Fully expanded leaves, lower surface: Close to 147B; venation, close to N144D.

*Petioles*.—Length: About 5 cm. Diameter: About 3 mm. Texture, upper surface: Moderately pubescent. Texture, lower surface: Densely pubescent. Color, upper and lower surfaces: Close to 144A.

Inflorescence description:

*Appearance*.—Composite inflorescence form with oblanceolate-shaped ray florets; solitary inflorescences borne on upright and strong scapes and held above the foliar plane; ray and disc florets arranged acropetally on a capitulum.

*Fragrance*.—None detected.

*Flowering season*.—Plants begin flowering about three months after planting; under garden conditions in The Netherlands, plants flower from spring to late summer; plants can be flowered year-round in the greenhouse.

*Inflorescence longevity*.—Depending on the temperature, inflorescences last about two to four weeks on the plant; inflorescences not persistent.

*Quantity of inflorescences*.—Freely flowering habit with about eleven open and developing inflorescences per plant at one time.

*Inflorescence buds*.—Height: About 1.9 cm. Diameter: About 2.2 cm. Shape: Flattened ovate. Color: Close to between 137C and 143A; immature ray florets, close to 151B to 151C.

*Inflorescence size*.—Diameter: About 5.9 cm. Depth (height): About 2.3 cm. Diameter of disc: About 2.4 cm. Receptacle height: About 2 mm. Receptacle diameter: About 4 mm.

*Receptacle color*.—Close to 145D.

*Ray florets*.—Quantity and arrangement: About 40 per inflorescence arranged in about two whorls. Orientation: About 50° from vertical. Length: About 2.9 cm. Width: About 7 mm. Shape: Oblanceolate. Apex: Finely emarginate to finely praemorse. Base: Cuneate. Margin: Entire. Texture, upper surface: Smooth, glabrous; velvety; slightly longitudinally ridged. Texture, lower surface: Smooth, glabrous; slightly velvety; longitudinally ridged. Color: When opening, upper surface: Close to N30B. When opening, lower surface: Close to 15B. Fully opened, upper surface: Close to N30C; towards the apex, tinged with close to 31A, color becoming closer to 22A and apex, close to 22B, with development. Fully opened, lower surface: Close to 15A tinged with close to 24B; color becoming closer to 15B with development.

*Disc florets*.—Quantity and arrangement: About 340 massed at center of receptacle. Length: About 1.2 cm. Width: About 5 mm. Shape: Tubular with upper two or three lobes free at the apex. Apex: Obtuse; upper 25%, free. Base: Lower 75%, fused. Margin, free lobes: Entire. Texture, upper and lower surfaces: Smooth, glabrous. Color, prior to opening: Apex and mid-section: Close to 150D. Base: Close to 157B. Color, when opening and fully opened: Apex: Close to 26B. Mid-section: Close to 11C. Base: Close to 150D.

*Pappus*.—Quantity of hairs per floret: About 50. Length: About 8 mm. Diameter: Less than 1 mm. Texture: Soft. Color: Close to 162D.

*Phyllaries*.—Quantity and arrangement: About 60 per inflorescence arranged in about three whorls. Length: About 1.4 cm. Width (at base): About 2 mm. Shape: Lanceolate. Apex: Narrowly acute. Base: Cuneate. Margin: Entire. Texture, upper surface: Smooth, glabrous. Texture, lower surface: Moderately tomentose. Color, upper surface: Close to 143C. Color, lower surface: Close to 137B to 137C.

*Scapes*.—Length: About 27.7 cm. Diameter: Proximally, about 5 mm; distally, about 4 mm. Angle: About 10° from vertical. Strength: Strong. Texture: Moderately tomentose. Color: Proximally, close to 143B slightly tinged with close to N199A; distally, close to 143A.

*Reproductive organs*.—Androecium (present on disc florets only): Quantity per floret: Five. Filament length: About 5 mm. Filament color: Close to 155D. Anther shape: Lanceolate. Anther length: About 4 mm. Anther color: Close to 12A and 13B. Pollen amount: Scarce. Pollen color: Close to 15A. Gynoecium (present only on ray florets): Quantity per floret: One. Pistil length: About 9 mm. Stigma shape: Cleft. Stigma color: Close to 13C. Style length: About 8.5 mm. Style color: Close to 13D. Ovary color: Close to 155A.

*Seeds and fruits*.—Seed and fruit production has not been observed on plants of the new *Gerbera*.

Disease & pest resistance: Resistance to pathogens and pests common to *Gerbera* plants has not been observed on plants of the new *Gerbera* grown under commercial production conditions.

Garden performance: Plants of the new *Gerbera* have been observed to have good garden performance and to tolerate high temperatures about 35° C. and to be cold hardy to USDA Hardiness Zone 7.

It is claimed:

1. A new and distinct *Gerbera* plant named 'Garkendall' as illustrated and described.

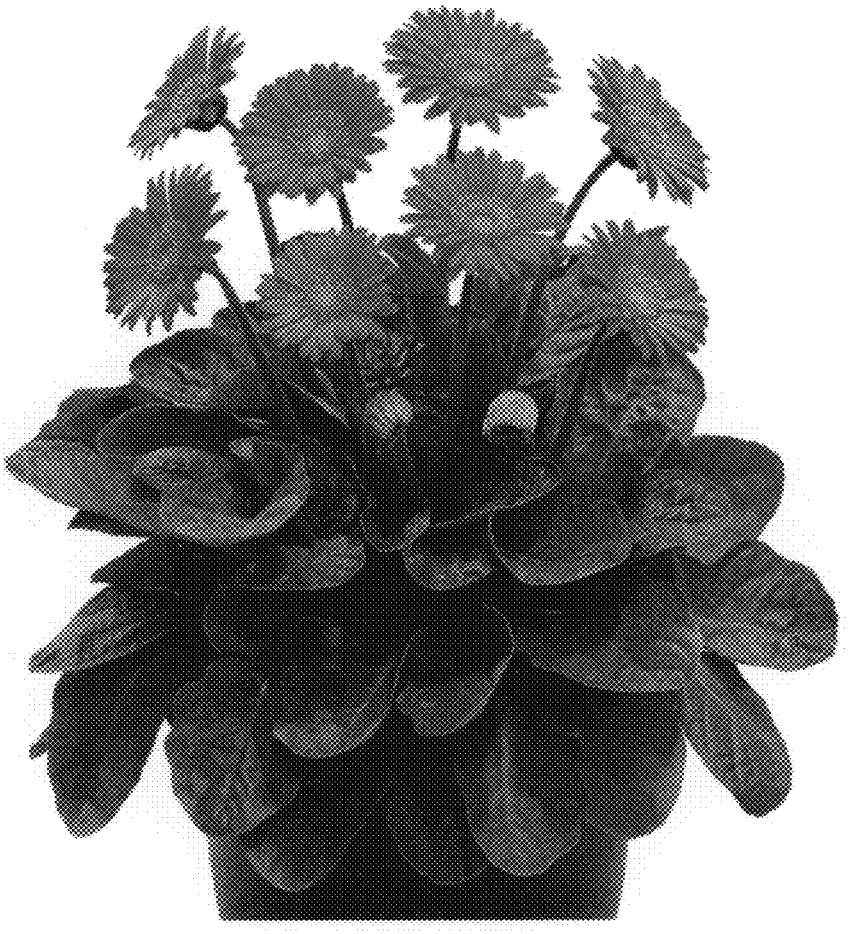

* * * * *